US007244277B2

(12) United States Patent
Kleen et al.

(10) Patent No.: US 7,244,277 B2
(45) Date of Patent: Jul. 17, 2007

(54) OXIDATION COLORANT IN A TUBE

(75) Inventors: Astrid Kleen, Hamburg (DE); Mustafa Akram, Hamburg (DE); Stefan Hoepfner, Hamburg (DE); Hartmut Manneck, Klein Wesenberg (DE)

(73) Assignee: Henkel Kommanditgesellschaft auf Aktien, Dusseldorf (DE)

( * ) Notice: Subject to any disclaimer, the term of this patent is extended or adjusted under 35 U.S.C. 154(b) by 0 days.

(21) Appl. No.: 11/455,434

(22) Filed: Jun. 19, 2006

(65) Prior Publication Data

US 2006/0277694 A1   Dec. 14, 2006

Related U.S. Application Data

(63) Continuation of application No. PCT/EP04/13940, filed on Dec. 8, 2004.

(30) Foreign Application Priority Data

Dec. 17, 2003   (DE)   ................ 103 59 557

(51) Int. Cl.
*A61K 7/13* (2006.01)
(52) U.S. Cl. .............. 8/405; 8/401; 8/408; 8/410; 8/412; 8/416; 8/421; 8/426
(58) Field of Classification Search .......... 8/405, 8/401, 408, 410, 412, 416, 421, 426
See application file for complete search history.

(56) References Cited

U.S. PATENT DOCUMENTS

| | | | |
|---|---|---|---|
| 2,019,576 A | 11/1935 | Mikaelson | |
| 3,753,968 A | 8/1973 | Ward | |
| 3,931,912 A | 1/1976 | Hsiung | |
| 4,184,844 A | 1/1980 | Grollier | |
| 4,237,253 A | 12/1980 | Jacquet | |
| 4,294,293 A | 10/1981 | Lorenz | |
| 4,324,780 A | 4/1982 | Jacquet | |
| 4,393,886 A | 7/1983 | Strasilla | |
| 4,725,282 A | 2/1988 | Hoch | |
| 4,814,101 A | 3/1989 | Schieferstein | |
| 4,865,774 A | 9/1989 | Fabry | |
| 4,931,218 A | 6/1990 | Schenker | |
| 5,061,289 A | 10/1991 | Clausen | |
| 5,136,093 A | 8/1992 | Smith | |
| 5,294,726 A | 3/1994 | Behler | |
| 5,380,340 A | 1/1995 | Neunhoeffer | |
| 5,480,459 A | 1/1996 | Mager | |
| 5,534,267 A | 7/1996 | Neunhoeffer | |
| 5,766,576 A | 6/1998 | Lowe | |
| 5,773,595 A | 6/1998 | Weuthen | |
| 6,099,592 A | 8/2000 | Vidal | |
| 6,179,881 B1 * | 1/2001 | Henrion et al. ............ | 8/407 |
| 6,284,003 B1 | 9/2001 | Rose | |
| 2003/0106167 A1 | 6/2003 | Rose | |
| 2003/0150069 A1 | 8/2003 | Kleen | |
| 2003/0167578 A1 | 9/2003 | Naumann | |
| 2004/0049860 A1 | 3/2004 | Cottard | |

FOREIGN PATENT DOCUMENTS

| | | |
|---|---|---|
| DE | 1 942 570 | 3/1970 |
| DE | 23 59 399 | 6/1975 |
| DE | 28 17 369 | 10/1978 |
| DE | 28 27 610 | 1/1980 |
| DE | 31 39 438 | 4/1983 |
| DE | 37 23 354 | 1/1989 |
| DE | 37 25 030 | 2/1989 |
| DE | 38 43 892 | 6/1990 |
| DE | 39 26 344 | 2/1991 |
| DE | 39 29 973 | 3/1991 |
| DE | 41 33 957 | 4/1993 |
| DE | 44 13 686 | 10/1995 |
| DE | 44 13 868 | 10/1995 |
| DE | 195 43 988 | 5/1997 |
| DE | 197 56 454 | 6/1999 |
| DE | 199 45 486 | 3/2001 |
| DE | 101 62 640 | 7/2003 |
| DE | 102 40 757 | 7/2003 |
| EP | 0 047 714 | 3/1982 |
| EP | 0 217 274 | 4/1987 |
| EP | 0 283 817 | 9/1988 |

(Continued)

OTHER PUBLICATIONS

Gutcho, M.H., et al., "Inorganic Pigments: Manufacturing Processes," Chemical Technology review No. 166, pp. 161-173, (1980) (ISBN: 0-8155-0811-5).
Buxbaum, G., et al., "Industrial inorganic pigments, 2 edition", Weinheim, VCH, pp. 211-231 (1998).
Zviak, C., ed., The Science of Hair Care, Chapter 7, pp. 248-250 vol. 7 "Dermatologie")(1986).
Zviak, C., ed., The Science of Hair Care, Chapter 8 pp. 264-267, vol. 7 "Dermatologie")(1986).
Website printout, Enterprise and Industry, "Cosmetics—Introduction", from the European Commission, dated Jan. 23, 2006.

(Continued)

*Primary Examiner*—Eisa Elhilo
(74) *Attorney, Agent, or Firm*—John E. Drach

(57) ABSTRACT

Keratinic fibers are colored by a two-component composition for coloring keratinous fibers comprising a first preparation (A) comprising at least one oxidation dye precursor and a second preparation (B) comprising at least one care component, wherein the two preparations are packaged separately from one another in the compartments of a two-compartment tube.

The compartment openings in the tube are oriented in such a way that the contents of each of the compartments are emitted simultaneously into a common space.

12 Claims, No Drawings

| | FOREIGN PATENT DOCUMENTS | |
|---|---|---|
| EP | 0 671 161 | 9/1995 |
| EP | 0 740 931 | 11/1996 |
| EP | 0 998 908 | 5/2000 |
| GB | 1 026 978 | 4/1966 |
| GB | 1 153 196 | 5/1969 |
| GB | 1 289 712 | 9/1972 |
| GB | 2 104 091 | 3/1983 |
| JP | 03-225052 | 10/1991 |
| WO | WO 86/00223 | 1/1986 |
| WO | WO 92/13829 | 8/1992 |
| WO | WO 93/23006 | 11/1993 |
| WO | WO 94/08969 | 4/1994 |
| WO | WO 94/08970 | 4/1994 |
| WO | WO 96/02162 | 2/1996 |
| WO | WO 96/15765 | 5/1996 |
| WO | WO 00/47714 | 8/2000 |
| WO | WO 01/97756 | 12/2001 |
| WO | WO 02/17274 | 2/2002 |
| WO | WO 02/45673 | 6/2002 |
| WO | WO 02/083817 | 10/2002 |
| WO | WO 03/089330 | 10/2003 |

OTHER PUBLICATIONS

Schrader, K-H., "Grundlagen und Rezepturen der Kosmetika," 2nd edition, table of contents Huthig Verlag, Heidelberg, (1989).
"International Cosmetic Ingredient Dictionary and Handbook," Seventh Ed., The Cosmetic, Toiletry and Fragrance Assn. Washington DC (1997).
Guideline for declaring the contents of cosmetic agents, published by Assn. of Personal Hygiene and Washing Agents Industry (1996).
U.S. Appl. No. 11/454,706, filed Jun. 15, 2006, Kleen.
U.S. Appl. No. 11/471,101, filed Jun. 19, 2006, Kleen.

* cited by examiner

OXIDATION COLORANT IN A TUBE

CROSS REFERENCE TO RELATED APPLICATIONS

This application is a continuation under 35 U.S.C. § 365(c) and 35 U.S.C. § 120 of International Application PCT/EP2004/013940, filed Dec. 8, 2004. This application also claims priority under 35 U.S.C. § 119 of DE 103 59 557.0, filed Dec. 17, 2003. Each application is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION (1) Field of the Invention

The present invention relates to a two-component composition for coloring keratin fibers which is formulated in a two-chamber tube, to a corresponding two-chamber tube, and to a method of coloring keratin fibers using this composition.

Human hair is nowadays treated in diverse ways with hair cosmetic preparations. These include, for example, cleansing the hair using shampoos, care and regeneration using rinses and treatments, as well as bleaching, coloring and shaping the hair using colorants, tints, waving compositions and styling preparations. In this regard, compositions for changing or nuancing the color of head hair play a prominent role.

For temporary colorations, use is usually made of colorants or tints which comprise so-called direct dyes as coloring component. These are dye molecules which attach directly to the hair and require no oxidative process to develop the color. These dyes include, for example, henna, which has been known since antiquity for coloring body and hair. These colorations are usually significantly more sensitive toward shampooing than the oxidative colorations, meaning that an often undesired nuance shift or even a visible "decoloration" arises very much more quickly.

For lasting, intense colorations with corresponding fastness properties, use is made of so-called oxidation colorants. Such colorants usually comprise oxidation dye precursors, so-called developer components and coupler components. Under the influence of oxidizing agents or of atmospheric oxygen, the developer components form the actual dyes with one another or with coupling with one or more coupler components. The oxidation colorants are characterized by excellent, long-lasting coloring results. For natural-looking colorations, a mixture of a relatively large number of oxidation dye precursors usually has to be used; in many cases, in addition, direct dyes are used for the nuancing.

Usually, hair colorants are formulated in the form of aqueous emulsions or coloring gels which, if appropriate, are mixed directly prior to application with a separately formulated oxidizing agent preparation. However, this method still leaves something to be desired with regard to the storage stability of the formulations, the doseability and ease of handling.

BRIEF SUMMARY OF THE INVENTION

Surprisingly, it has now been found that storage-stable colorants are obtained if the actual colorant and the oxidizing agent preparation are formulated separately from one another in a two-chamber tube.

Therefore, the present invention first provides two-component compositions for coloring keratin fibers, comprising a first preparation (A) comprising at least one oxidation dye precursor, and a second preparation (B) comprising at least one oxidizing agent, where the two preparations are formulated separately from one another in the chambers of a two-chamber tube.

BRIEF DESCRIPTION OF THE SEVERAL VIEWS OF THE DRAWING(S)

Not Applicable

DETAILED DESCRIPTION OF THE INVENTION

The two-component compositions according to the invention are characterized by exceptional care and coloring performance and high stability. Moreover, it is ensured that the consumer applies the components in the mixing ratio intended by the manufacturer. In this way, on the one hand the product safety is increased and, on the other hand, it is ensured that the product produces the desired effect.

In a first preferred embodiment, the preparation (A) comprises at least one developer component. The developer components used are usually primary aromatic amines with a further free or substituted hydroxy or amino group located in the para or ortho position, diaminopyridine derivatives, heterocyclic hydrazones, 4-aminopyrazole derivatives, and 2,4,5,6-tetraaminopyrimidine and derivatives thereof.

According to the invention, it may be preferred to use a p-phenylenediamine derivative or one of its physiologically compatible salts as developer component. Particular preference is given to p-phenylenediamine derivatives of the formula (E1)

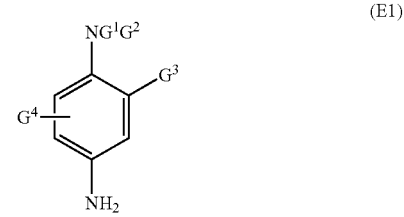

where
$G^1$ is a hydrogen atom, a $C_1$- to $C_4$-alkyl radical, a $C_1$- to $C_4$-monohydroxyalkyl radical, a $C_2$- to $C_4$-polyhydroxyalkyl radical, a ($C_1$- to $C_4$)alkoxy($C_1$- to $C_4$)alkyl radical, a 4'-aminophenyl radical or a $C_1$- to $C_4$-alkyl radical which is substituted by a nitrogen-containing group, a phenyl radical or a 4'-aminophenyl radical;
$G^2$ is a hydrogen atom, a $C_1$- to $C_4$-alkyl radical, a $C_1$- to $C_4$-monohydroxyalkyl radical, a $C_2$- to $C_4$-polyhydroxyalkyl radical, a (C$_1$- to C$_4$)alkoxy(C$_1$- to C$_4$)alkyl radical or a C$_1$- to C$_4$-alkyl radical which is substituted by a nitrogen-containing group;

G$^3$ is a hydrogen atom, a halogen atom, such as a chlorine, bromine, iodine or fluorine atom, a C$_1$- to C$_4$-alkyl radical, a C$_1$- to C$_4$-monohydroxyalkyl radical, a C$_2$- to C$_4$-polyhydroxyalkyl radical, a C$_1$- to C$_4$-hydroxyalkoxy radical, a C$_1$- to C$_4$-acetylaminoalkoxy radical, a C$_1$- to C$_4$-mesylaminoalkoxy radical or a C$_1$- to C$_4$-carbamoylaminoalkoxy radical;

G$^4$ is a hydrogen atom, a halogen atom or a C$_1$- to C$_4$-alkyl radical or if G$^3$ and G$^4$ are in the ortho position relative to one another, they can together form a bridging α,ω-alkylenedioxo group, such as, for example, an ethylenedioxy group.

Examples of the C$_1$- to C$_4$-alkyl radicals specified as substituents in the compounds according to the invention are the groups methyl, ethyl, propyl, isopropyl and butyl. Ethyl and methyl are preferred alkyl radicals. C$_1$- to C$_4$-alkoxy radicals preferred according to the invention are, for example, a methoxy or an ethoxy group. In addition, preferred examples of a C$_1$- to C$_4$-hydroxyalkyl group which may be specified are a hydroxymethyl group, a 2-hydroxyethyl group, a 3-hydroxypropyl group or a 4-hydroxybutyl group. A 2-hydroxyethyl group is particularly preferred. A particularly preferred C$_2$- to C$_4$-polyhydroxyalkyl group is the 1,2-dihydroxyethyl group. According to the invention, examples of halogen atoms are F, Cl or Br atoms, Cl atoms are very particularly preferred. According to the invention, the other terms used are derived from the definitions given here. Examples of nitrogen-containing groups of the formula (E1) are in particular the amino groups, C$_1$- to C$_4$-monoalkylamino groups, C$_1$- to C$_4$-dialkylamino groups, C$_1$- to C$_4$-trialkylammonium groups, C$_1$- to C$_4$-monohydroxyalkylamino groups, imidazolinium and ammonium.

Particularly preferred p-phenylenediamines of the formula (E1) are chosen from p-phenylenediamine, p-tolylenediamine, 2-chloro-p-phenylenediamine, 2,3-dimethyl-p-phenylenediamine, 2,6-dimethyl-p-phenylenediamine, 2,6-dyethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis(β-hydroxyethyl)-p-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-p-phenylenediamine, 2-(α,β-dihydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl,β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-(β-methoxyethyl)-p-phenylenediamine, 5,8-diaminobenzo-1,4-dioxane and their physiologically compatible salts.

According to the invention, very particularly preferred p-phenylenediamine derivatives of the formula (E1) are p-phenylenediamine, p-tolylenediamine, 2-(β-hydroxyethyl)-p-phenylenediamine, 2-(α,β-dihydroxyethyl)-p-phenylenediamine and N,N-bis(β-hydroxyethyl)-p-phenylenediamine.

According to the invention, it may also be preferred to use compounds which comprise at least two aromatic nuclei which are substituted by amino and/or hydroxyl groups as developer component.

Among the binuclear developer components which can be used in the coloring compositions according to the invention, specific mention may be made of the compounds which conform to the following formula (E2), and to their physiologically compatible salts:

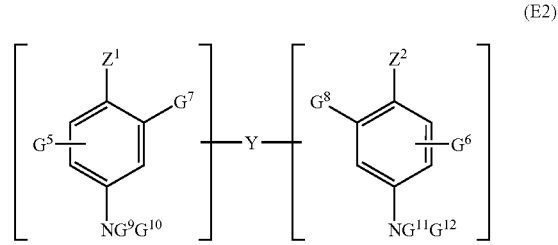

(E2)

where:

Z$^1$ and Z$^2$, independently of one another, are a hydroxyl or NH$_2$ radical, which is optionally substituted by a C$_1$- to C$_4$-alkyl radical, by a C$_1$- to C$_4$-hydroxyalkyl radical and/or by a bridge Y or which is optionally part of a bridging ring system, the bridge Y is an alkylene group having 1 to 14 carbon atoms, such as, for example, a linear or branched alkylene chain or an alkylene ring, which may be interrupted or terminated by one or more nitrogen-containing groups and/or one or more hetero atoms, such as oxygen, sulfur or nitrogen atoms, and may possibly be substituted by one or more hydroxyl radicals or C$_1$- to C$_8$-alkoxy radicals, or a direct bond, G$^5$ and G$^6$, independently of one another, are a hydrogen or halogen atom, a C$_1$- to C$_4$-alkyl radical, a C$_1$- to C$_4$-monohydroxyalkyl radical, a C$_2$- to C$_4$-polyhydroxyalkyl radical, a C$_1$- to C$_4$-aminoalkyl radical or a direct bond to the bridge Y, G$^7$, G$^8$, G$^9$, G$^{10}$, G$^{11}$ and G$^{12}$, independently of one another, are a hydrogen atom, a direct bond to the bridge Y or a C$_1$- to C$_4$-alkyl radical, provided that the compounds of the formula (E2) comprise only one bridge Y per molecule and the compounds of the formula (E2) comprise at least one amino group which carries at least one hydrogen atom.

According to the invention, the substituents used in formula (E2) are defined analogously to the above statements.

Preferred binuclear developer components of the formula (E2) are, in particular: N,N'-bis(β-hydroxyethyl)-N,N'-bis(4'-aminophenyl)-1,3-diaminopropan-2-ol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methyl-aminophenyl)tetramethylenediamine, N,N'-diethyl-N,N'-bis(4'-amino-3'-methyl-phenyl)ethylenediamine, bis(2-hydroxy-5-aminophenyl)methane, 1,3-bis(2,5-diaminophenoxy)propan-2-ol, N,N'-bis(4'-aminophenyl)-1,4-diazacycloheptane, N,N'-bis(2-hydroxy-5-aminobenzyl)piperazine, N-(4'-aminophenyl)-p-phenylenediamine and 1,10-bis(2',5'-diaminophenyl)-1,4,7,10-tetraoxadecane and their physiologically compatible salts.

Particularly preferred binuclear developer components of the formula (E2) are N,N'-bis(β-hydroxyethyl)-N,N'-bis(4'-aminophenyl)-1,3-diaminopropan-2-ol, bis(2-hydroxy-5-aminoph 1,3-bis(2,5-diaminophenoxy)propan-2-ol, N,N'-bis (4'-aminophenyl)-1,4-diazacycloheptane and 1,10-bis(2',5'-diaminophenyl)-1,4,7,10-tetraoxadecane or one of their physiologically compatible salts.

Bis(2-hydroxy-5-aminophenyl)methane is a very particularly preferred binuclear developer component of the formula (E2).

In addition, it may be preferred according to the invention to use a p-aminophenol derivative or one of its physiologically compatible salts as developer component. Particular preference is given to p-aminophenol derivatives of the formula (E3)

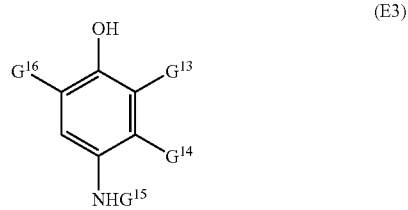

where:
$G^{13}$ is a hydrogen atom, a halogen atom, a $C_1$- to $C_4$-alkyl radical, a $C_1$- to $C_4$-monohydroxyalkyl radical, a $C_2$- to $C_4$-polyhydroxyalkyl radical, a ($C_1$- to $C_4$)alkoxy($C_1$- to $C_4$)alkyl radical, a $C_1$- to $C_4$-aminoalkyl radical, a hydroxy($C_1$- to $C_4$)alkylamino radical, a $C_1$- to $C_4$-hydroxyalkoxy radical, a $C_1$- to $C_4$-hydroxyalkyl($C_1$- to $C_4$)aminoalkyl radical or a (di-$C_1$- to $C_4$-alkylamino)($C_1$- to $C_4$)alkyl radical, and $G^{14}$ is a hydrogen or halogen atom, a $C_1$- to $C_4$-alkyl radical, a $C_1$- to $C_4$-monohydroxyalkyl radical, a $C_2$- to $C_4$-polyhydroxyalkyl radical, a ($C_1$- to $C_4$)alkoxy($C_1$- to $C_4$)alkyl radical, a $C_1$- to $C_4$-aminoalkyl radical or a $C_1$- to $C_4$-cyanoalkyl radical, $G^{15}$ is hydrogen, a $C_1$- to $C_4$-alkyl radical, a $C_1$- to $C_4$-monohydroxyalkyl radical, a $C_2$- to $C_4$-polyhydroxyalkyl radical, a phenyl radical or a benzyl radical, and $G^{16}$ is hydrogen or a halogen atom.

According to the invention, the substituents used in formula (E3) are defined analogously to the above statements.

Preferred p-aminophenols of the formula (E3) are, in particular, p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(β-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-(α,β-dihydroxyethyl)phenol, 4-amino-2-fluorophenol, 4-amino-2-chlorophenol, 4-amino-2,6-dichlorophenol, 4-amino-2-(diethylaminomethyl)phenol and their physiologically compatible salts.

Very particularly preferred compounds of the formula (E3) are p-aminophenol, 4-amino-3-methylphenol, 4-amino-2-aminomethylphenol, 4-amino-2-(α,β-dihydroxyethyl)phenol and 4-amino-2-(diethylaminomethyl)phenol.

In addition, the developer component can be chosen from o-aminophenol and its derivatives, such as, for example, 2-amino-4-methylphenol, 2-amino-5-methylphenol or 2-amino-4-chlorophenol.

In addition, the developer component can be chosen from heterocyclic developer components, such as, for example, the pyridine, pyrimidine, pyrazole, pyrazolepyrimidine derivatives and their physiologically compatible salts.

Preferred pyridine derivatives are, in particular, the compounds which are described in the patents GB 1 026 978 and GB 1 153 196, such as 2,5-diaminopyridine, 2-(4'-methoxyphenyl)amino-3-aminopyridine, 2,3-diamino-6-methoxypyridine, 2-(β-methoxyethyl)amino-3-amino-6-methoxypyridine and 3,4-diaminopyridine.

Preferred pyrimidine derivatives are, in particular, the compounds which are described in the German patent DE 2 359 399, the Japanese laid-open specification JP 02019576 A2 or in the laid-open specification WO 96/15765, such as 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine.

Preferred pyrazole derivatives are, in particular, the compounds which are described in the patents DE 3 843 892, DE 4 133 957 and patent applications WO 94/08969, WO 94/08970, EP-740 931 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(β-aminoethyl)amino-1,3-dimethylpyrazole, 3,4,5-tri-aminopyrazole, 1-methyl-3,4,5-triaminopyrazole, 3,5-diamino-1-methyl-4-methylaminopyrazole and 3,5-diamino4-(β-hydroxyethyl) amino-1-methylpyrazole.

Preferred pyrazolepyrimidine derivatives are, in particular, the derivatives of pyrazole[1,5-a]pyrimidine of the following formula (E4) and tautomeric forms thereof if there is a tautomeric equilibrium:

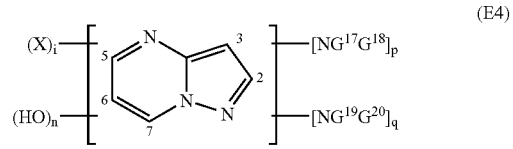

where:
$G^{17}$, $G^{18}$, $G^{19}$ and $G^{20}$, independently of one another, are a hydrogen atom, a $C_1$- to $C_4$-alkyl radical, an aryl radical, a $C_1$- to $C_4$-hydroxyalkyl radical, a $C_2$- to $C_4$-polyhydroxyalkyl radical, a ($C_1$- to $C_4$)alkoxy($C_1$- to $C_4$)alkyl radical, a $C_1$- to $C_4$-aminoalkyl radical, which may optionally be protected by an acetylureido or a sulfonyl radical, a ($C_1$- to $C_4$)alkylamino($C_1$- to $C_4$)alkyl radical, a di[($C_1$- to $C_4$)alkyl]($C_1$- to $C_4$)aminoalkyl radical, where the dialkyl radicals optionally form a carbocycle or a heterocycle with 5 or 6 chain members, a $C_1$- to $C_4$-hydroxyalkyl or a di($C_1$- to $C_4$)[hydroxyalkyl]($C_1$- to $C_4$)aminoalkyl radical, the X radicals, independently of one another, are a hydrogen atom, a $C_1$- to $C_4$-alkyl radical, an aryl radical, a $C_1$- to $C_4$-hydroxyalkyl radical, a $C_2$- to $C_4$- polyhydroxyalkyl radical, a $C_1$- to $C_4$-aminoalkyl radical, a ($C_1$- to $C_4$)alkylamino($C_1$- to $C_4$)alkyl radical, a di[($C_1$- to $C_4$)alkyl]($C_1$- to $C_4$)aminoalkyl radical, where the dialkyl radicals optionally form a carbocycle or a heterocycle having 5 or 6 chain members, a $C_1$- to $C_4$-hydroxyalkyl or a di($C_1$- to $C_4$-hydroxyalkyl)aminoalkyl radical, an amino radical, a $C_1$- to $C_4$-alkyl or di($C_1$- to $C_4$-hydroxyalkyl)amino radical, a halogen atom, a carboxylic acid group or a sulfonic acid group, i has the value 0, 1, 2 or 3,
p has the value 0 or 1,
q has the value 0 or 1 and
n has the value 0 or 1, provided that
the sum of p+q does not equal 0,
if p+q is 2, n has the value 0, and the groups $NG^{17}G^{18}$ and $NG^{19}G^{20}$ occupy positions (2,3); (5,6); (6,7); (3,5) or (3,7);
if p+q is 1, n has the value 1, and the groups $NG_{17}G_{18}$ (or $NG_{19}G_{20}$) and the group OH occupy positions (2,3); (5,6); (6,7); (3,5) or (3,7).

According to the invention, the substituents used in formula (E4) are defined analogously to the above statements.

If the pyrazole[1,5-a]pyrimidine of the above formula (E4) comprises a hydroxy group at one of positions 2, 5 or 7 of the ring system, there is a tautomeric equilibrium, which is represented, for example, in the following scheme:

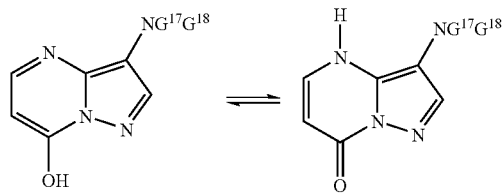

Among the pyrazole[1,5-a]pyrimidines of the above formula (E4), particular mention may be made of:
pyrazole[1,5-a]pyrimidine-3,7-diamine;
2,5-dimethylpyrazole[1,5-a]pyrimidine-3,7-diamine;
pyrazole[1,5-a]pyrimidine-3,5-diamine;
2,7-dimethylpyrazole[1,5-a]pyrimidine-3,5-diamine;
3-aminopyrazole[1,5-a]pyrimidin-7-ol;
3-aminopyrazole[1,5-a]pyrimidin-5-ol;
2-(3-aminopyrazole[1,5-a]pyrimidin-7-ylamino)ethanol;
2-(7-aminopyrazole[1,5-a]pyrimidin-3-ylamino)ethanol;
2-[(3-aminopyrazole[1,5-a]pyrimidin-7-yl)(2-hydroxyethyl)amino]ethanol;
2-[(7-aminopyrazole[1,5-a]pyrimidin-3-yl)(2-hydroxyethyl)amino]ethanol;
5,6-dimethylpyrazole[1,5-a]pyrimidine-3,7-diamine;
2,6-dimethylpyrazole[1,5-a]pyrimidine-3,7-diamine;
3-amino-7-dimethylamino-2,5-dimethylpyrazole[1,5-a]-pyrimidine;

and their physiologically compatible salts and their tautomeric forms if a tautomeric equilibrium is present.

As described in the literature, the pyrazole[1,5-a]pyrimidines of the above formula (E4) can be prepared by cyclization starting from an aminopyrazole or from hydrazine.

In a further preferred embodiment of the two-component composition according to the invention, the preparation (A) comprises at least one coupler component.

The coupler components used are usually m-phenylenediamine derivatives, naphthols, resorcinol and resorcinol derivatives, pyrazolones and m-aminophenol derivatives. Suitable coupler substances are, in particular, 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methylpyrazolone-5, 2,4-dichloro-3-aminophenol, 1,3-bis(2',4'-diaminophenoxy)propane, 2-chlororesorcinol, 4-chlororesorcinol, 2-chloro-6-methyl-3-aminophenol, 2-amino-3-hydroxypyridine, 2-methylresorcinol, 5-methylresorcinol and 2-methyl-4-chloro-5-aminophenol.

Coupler components preferred according to the invention are
m-aminophenol and derivatives thereof, such as, for example, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methyl 5-amino-4-chloro-2-methylphenol, 5-amino-4-methoxy-2-methylphenol, 5-(2'-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol and 2,4-dichloro-3-aminophenol,
o-aminophenol and derivatives thereof,
m-diaminobenzene and derivatives thereof, such as, for example, 2,4-diaminophenoxyethanol, 1,3-bis(2',4'-diaminophenoxy)propane, 1-methoxy-2-amino-4-(2'-hydroxyethylamino)benzene, 1,3-bis(2',4'-diaminophenyl)propane, 2,6-bis(2'-hydroxyethylamino)-1-methylbenzene and 1-amino-3-bis(2'-hydroxyethyl)aminobenzene,
o-diaminobenzene and derivatives thereof, such as, for example, 3,4-diaminobenzoic acid and 2,3-diamino-1-methylbenzene,
di- or trihydroxybenzene derivatives, such as, for example, resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene,
pyridine derivatives, such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine and 3,5-diamino-2,6-dimethoxypyridine,
naphthalene derivatives, such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene,
morpholine derivatives, such as, for example, 6-hydroxybenzomorpholine and 6-aminobenzomorpholine,
quinoxaline derivatives, such as, for example, 6-methyl-1,2,3,4-tetrahydroquinoxaline,
pyrazole derivatives, such as, for example, 1-phenyl-3-methylpyrazol-5-one,
indole derivatives, such as, for example, 4-hydroxyindole, 6-hydroxyindole and 7-hydroxyindole,
pyrimidine derivatives, such as, for example, 4,6-diaminopyridine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine or methylenedioxybenzene derivatives, such as, for example, 1-hydroxy-3,4-methylenedioxybenzene, 1-amino-3,4-methylenedioxybenzene and 1-(2'-hydroxyethyl)amino-3,4-methylenedioxybenzene.

Coupler components which are particularly preferred according to the invention are 1-naphthol, 1,5-, 2,7- and 1,7-dihydroxynaphthalene, 3-aminophenol, 5-amino-2-methylphe 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol and 2,6-dihydroxy-3,4-dimethylpyridine.

Within the scope of the present invention, it may be particularly preferred if the preparation (A) comprises at least one developer component chosen from p-phenylenediamine, p-tolulenediamine, p-aminophenol, N,N-bis(2-hydroxyethyl)-p-phenylenediamine, 1-(2-hydroxyethyl)-2,5-diaminobenzene, 3-methyl-4-aminophenol, bis(2-hydroxy-5-aminophenyl)methane, 2,4,5,6-tetraaminopyrimidine and 1-(2-hydroxyethyl)-4,5-diaminopyrazol and/or at least one further coupler component chosen from 2-(2,4-diaminophenoxy)ethanol, 1,3-bis(2,4-diaminophenoxy)propane, 5-amino-2-methylphenol, 2-amino-3-hydroxypyridine, resorcinol, 2-methylresorcinol, 4-chlororesorcinol, 2-amino-4-(2-hydroxyethylamino)anisole, 2,7-dihydroxynaphthalene and 3-aminophenol.

The developer components and the coupler components are preferably present in the preparation (A) in an amount of from 0.005 to 20% by weight, preferably 0.1 to 5% by weight, in each case based on the total two-component composition. Here, developer components and coupler components are generally used in approximately molar amounts relative to one another. Although the molar use has proven expedient, a certain excess of individual oxidation dye precursors is not disadvantageous, meaning that developer components and coupler components may be present in a molar ratio of from 1:0.5 to 1:3, in particular 1:1 to 1:2.

In addition, according to the invention, the preparation (A) can comprise a precursor of a nature-analogous dye. The precursors of nature-analogous dyes used are preferably those indoles and indolines which have at least one hydroxy or amino group, preferably as substituent on the six-membered ring. These groups can carry further substituents, e.g., in the form of an etherification or esterification of the hydroxy group or an alkylation of the amino group. In a second preferred embodiment, the colorants comprise at least one indole and/or indoline derivative.

Particularly well-suited as precursors of nature-analogous hair dyes are derivatives of the 5,6-dihydroxyindoline of the formula (Ia),

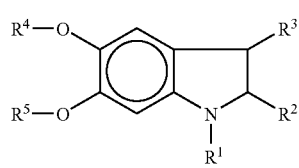

(Ia)

in which, independently of one another,
$R^1$ is hydrogen, a $C_1$–$C_4$-alkyl group or a $C_1$–$C_4$-hydroxyalkyl group, $R^2$ is hydrogen or a —COOH group, where the —COOH group can also be present as a salt with a physiologically compatible cation,
$R^3$ is hydrogen or a $C_1$–$C_4$-alkyl group,
$R^4$ is hydrogen, a $C_1$–$C_4$-alkyl group or a group —CO—$R^6$, in which $R^6$ is a $C_1$–$C_4$-alkyl group, and
$R^5$ is one of the groups given under $R^4$, and physiologically compatible salts of these compounds with an organic or inorganic acid.

Particularly preferred derivatives of indoline are 5,6-dihydroxyindoline, N methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid and 6-hydroxyindoline, 6-aminoindoline and 4-aminoindoline.

Within this group, particular emphasis is given to N-methyl-5,6-dihydroxyindoline, N-ethyl-5,6-dihydroxyindoline, N-propyl-5,6-dihydroxyindoline, N-butyl-5,6-dihydroxyindoline and in particular 5,6-dihydroxyindoline.

Exceptionally suitable precursors of nature-analogous hair dyes are also derivatives of the 5,6-dihydroxyindole of the formula (Ib),

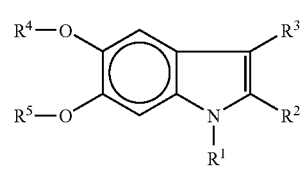

(Ib)

in which, independently of one another,
$R^1$ is hydrogen, a $C_1$–$C_4$-alkyl group or a $C_1$–$C_4$-hydroxyalkyl group,
$R^2$ is hydrogen or a —COOH group, where the —COOH group may also be present as a salt with a physiologically compatible cation,
$R^3$ is hydrogen or a $C_1$–$C_4$-alkyl group,
$R^4$ is hydrogen, a $C_1$–$C_4$-alkyl group or a group —CO—$R^6$, in which $R^6$ is a $C_1$–$C_4$-alkyl group, and
$R^5$ is one of the groups given under $R^4$, and physiologically compatible salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group, emphasis is given to N-methyl-5,6-dihydroxyindole, N-ethyl-5,6-dihydroxyindole, N-propyl-5,6-dihydroxyindole, N-butyl-5,6-dihydroxyindole, and in particular 5,6-dihydroxyindole.

The indoline and indole derivatives can be used in the two-component compositions according to the invention either as free bases or in the form of their physiologically compatible salts with inorganic or organic acids, e.g., the hydrochlorides, the sulfates and hydrobromides. The indole or indoline derivatives are usually present in these in amounts of 0.05–10% by weight, preferably 0.2–5% by weight, in each case based on the total two-component composition.

In a further embodiment, it may be preferred according to the invention to use the indoline or indole derivative in hair colorants in combination with at least one amino acid or an oligopeptide. The amino acid is advantageously an α-amino acid; very particularly preferred α-amino acids are arginine, ornithine, lysine, serine and histidine, in particular arginine.

According to the invention, besides the developer components and/or the coupler components, the preparation (A) can comprise one or more direct dyes for the nuancing. Direct dyes are usually nitrophenylenediamines, nitroaminophenols, azo dyes, anthraquinones or indophenols. Preferred direct dyes are the compounds known under the international names or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 11, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, and 1,4-diamino-2-nitrobenzene, 2-amino-4-nitrophenol, 1,4-bis(β-hydroxyethyl)amino-2-nitrobenzene, 3-nitro-4-(β-hydroxyethyl)aminophenol 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-1-hydroxy-4-nitrobenzene.

In a preferred embodiment of the present invention, the preparation (A) comprises a cationic direct dye. Particular preference is given here to (a) cationic triphenylmethane dyes, such as, for example, Basic Blue 7, Basic Blue 26, Basic Violet 2 and Basic Violet 14, (b) aromatic systems which are substituted by a quaternary nitrogen group, such as, for example, Basic Yellow 57, Basic Red 76, Basic Blue 99, Basic Brown 16 and Basic Brown 17, and (c) direct dyes which comprise a heterocycle which has at least one quaternary nitrogen atom, as are specified, for example, in EP-A2-998 908, which is hereby incorporated explicitly by reference, in claims 6 to 11.

Preferred cationic direct dyes of group (c) are, in particular, the following compounds:

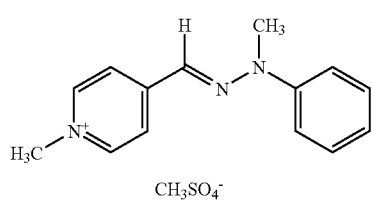
(DZ1)

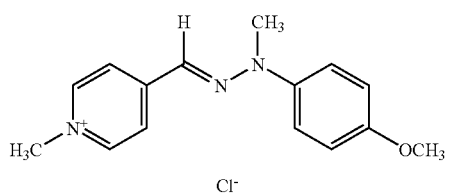
(DZ2)

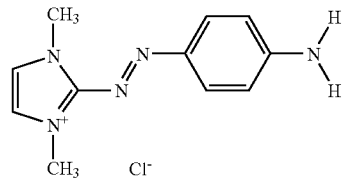
(DZ3)

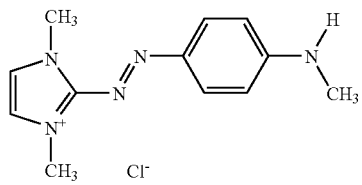
(DZ4)

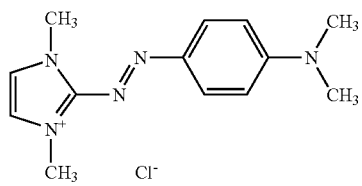
(DZ5)

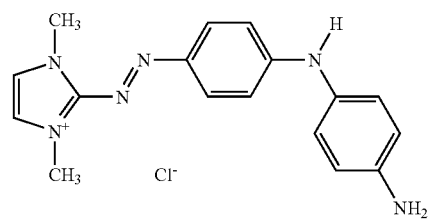
(DZ6)

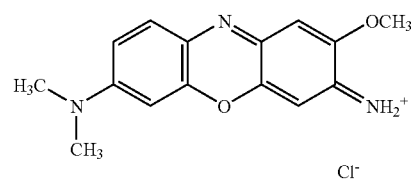
(DZ7)

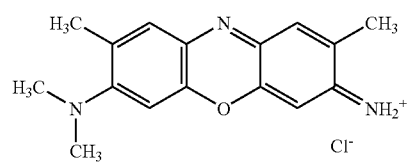
(DZ8)

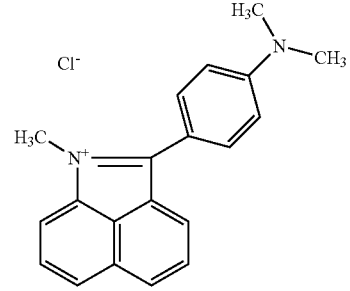
(DZ9)

The compounds of the formulae (DZ1), (DZ3) and (DZ5), which are also known under the names Basic Yellow 87, Basic Orange 31 and Basic Red 51, are very particularly preferred cationic direct dyes of group (c).

The cationic direct dyes which are sold under the trade name Arianor® are likewise very particularly preferred cationic direct dyes according to the invention.

According to this embodiment, the compositions according to the invention comprise the direct dyes preferably in an amount of from 0.01 to 20% by weight, based on the total two-component composition.

In addition, the preparations according to the invention can also comprise dyes which occur in nature, as are present, for example, in henna red, henna neutral, henna black, chamomile blossom, sandalwood, black tea, buckthorn bark, sage, logwood, madder root, catechu, sedre and alkanna root.

It is not necessary for the oxidation dye precursors or the direct dyes to each constitute uniform compounds. Rather, it is possible that, as a result of the preparation processes for the individual dyes, further components are present in minor amounts in the hair colorants according to the invention provided these do not adversely affect the coloring result or have to be excluded for other reasons, e.g., toxicological reasons.

With regard to the dyes which can be used in the hair colorants and tints according to the invention, reference is also made expressly to the monograph by Ch. Zviak, The Science of Hair Care, chapter 7 (pages 248–250; direct dyes), and chapter 8, pages 264–267; oxidation dye precursors), published as volume 7 of the "Dermatology" series (editors: Ch. Culnan and H. Maibach), Verlag Marcel Dekker Inc., New York, Basle, 1986, and the "European Inventory of Cosmetic Raw Materials," published by the European Community, available in diskette form from the Bundesverband Deutscher Industrie- und Handelsunternehmen für Arzneimittel, Reformwaren und Körperpflegemittel e.V., Mannheim.

In addition, the two-component compositions according to the invention comprise, in the preparation (B), at least one oxidizing agent as constituent essential to the invention.

Within the scope of a first preferred embodiment, the preparation (B) comprises at least one chemical oxidizing agent. Suitable chemical oxidizing agents are persulfates, chlorites and, in particular, hydrogen peroxide or its addition products onto urea, melamine, and sodium borate. Hydrogen peroxide is a very particularly preferred chemical oxidizing agent according to the invention.

Within the scope of a second preferred embodiment, the preparation (B) comprises, as oxidizing agent, at least one enzyme which can catalyze the oxidation of the dye precursors. Although in principle all of the enzymes which are able to catalyze this process are suitable according to the invention, enzymes which have proven to be particularly suitable are those which
(i) produce small amounts of hydrogen peroxide in situ,
(ii) directly oxidize the dye precursors with the help of atmospheric oxygen or
(iii) accelerate the oxidation of the dye precursors through hydrogen peroxide.

The behavior described under (i) is typically displayed by oxidases which react with their particular substrate to form hydrogen peroxide. Examples of such enzymes are glucose oxidase (EC No. 1.1.3.4), alcohol oxidase (EC No. 1.1.3.13), oxidase for secondary alcohols (EC No. 1.1.3.18), oxidase for long-chain alcohols (EC No. 1.1.3.20), glycerol-3-phosphate oxidase (EC No. 1.1.3.21), glycolate oxidase (EC No. 1.1.3.15), methanol oxidase (EC No. 1.1.3.31), vanillyl alcohol oxidase (EC No. 1.1.3.38), pyruvate oxidase (EC No. 1.2.3.3), oxalate oxidase (EC No. 1.2.3.4), cholesterol oxidase (EC No. 1.1.3.6), uricase (EC No. 1.7.3.3), lactate oxidase (EC No. 1.13.12.4), xanthine oxidase (EC No. 1.1.3.22), pyranose oxidase (EC No. 1.1.3.10), amino acid oxidases (EC No. 1.4.3.2, EC No. 1.4.3.3), acyl-CoA oxidase (EC No. 1.3.3.6), glutamate oxidases (EC No. 1.4.3.7, EC No. 1.4.3.11), protein-lysine-6 oxidase (EC No. 1.4.3.14), lysine oxidase (EC No. 1.4.3.14), sulfite oxidase (EC No. 1.8.3.1), catechol oxidase (EC No. 1.10.3.1), L-ascorbate oxidase (EC No. 1.10.3.3), choline oxidase (EC No. 1.1.3.17), monoamine oxidase (EC No. 1.4.3.4), diamine oxidase (EC No. 1.4.3.6), sarcosine oxidase (EC No. 1.5.3.1), and galactose oxidase (EC No. 1.1.3.9). Particularly preferred examples of such oxidases are uricase, glucose oxidase, and choline oxidase. Uricase is a very particularly preferred enzyme of class (i). So that these enzymes can catalyze the coloring process, the compositions according to the invention must always comprise the corresponding substrates in an adequate amount.

Enzymes which directly oxidize the dye precursors with the help of atmospheric oxygen, (ii), are, for example, the laccases (EC No. 1.10.3.2), the tyrosinases (EC No. 1.10.3.1), ascorbate oxidase (EC No. 1.10.3.3), the bilirubin oxidases (EC No. 1.3.3.5), and phenol oxidases of the type Acremonia, Stachybotrys or Pleurotus. According to the invention, the laccases are very particularly preferred enzymes of class (ii).

Category (iii) of the enzymes preferred according to the invention includes the peroxidases (EC No. 1.11.1.7). These allow colorations even with small amounts of hydrogen peroxide. Here, it is unimportant whether small amounts of hydrogen peroxide are incorporated into the formulation or whether it is formed in situ by the enzymes listed under (i). According to the invention, particular preference is given to the peroxidase that can be obtained from horseradish.

The enzyme is preferably used in an amount of 0.0001–1% by weight, based on the amount of protein in the enzyme and the total two-component composition.

Within the scope of a third preferred embodiment, the preparation (B) comprises, as oxidizing agent, at least one oxidation catalyst, such as, for example, metal ions, iodides or quinones. Within the scope of this embodiment, the catalysts can accelerate the oxidation of the dye precursors through atmospheric oxygen. However, it is also conceivable that the catalysts accelerate the oxidation through a chemical oxidizing agent which is present. Within the scope of the last-mentioned embodiment, on the one hand the reaction rate can be increased or, on the other hand, the concentration of the chemical oxidizing agents used can be decreased.

Suitable metal ions are, for example, $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$. Of particularly suitability here are $Zn^{2+}$, $Cu^{2+}$ and $Mn^{2+}$. The metal ions can in principle be used in the form of any physiologically compatible salt or in the form of a complex compound. Preferred salts are the acetates, sulfates, halides, lactates and tartrates. By using these metal salts, it is possible to both accelerate the development of the coloration, and also to influence the color nuance in a targeted manner.

The two-component composition according to the invention is formulated in different chambers of a multichamber tube. The multichamber tube is preferably a two-chamber tube, with a first chamber accommodating preparation (A), and a second chamber accommodating preparation (B). However, it is also possible to use a multichamber tube which has more than two chambers, for example, three or four chambers. In this case, preparation (A) and/or preparation (B) can be divided between two or more chambers of the multichamber tube, in which case it must be ensured that exclusively preparation (A) or preparation (B) is located in a particular chamber.

Two-chamber tubes are already known in principle in the prior art. In a particularly simple embodiment, the tubes have two separate chambers which are constructed as concentric tubes. These define the inner and outer chamber and end in a common head or exit region. The head region is configured in such a way that the two preparations exit from the tube together as soon as pressure is exerted thereon. The configuration of the head region determines in what stripe pattern the preparations exit from the tube. The known standard commercial tubes have an equal ratio of the volumes of the inside tube to the outside tube and thus a mixing ratio of 50:50. For products whose two phases have to be stored separately and whose mixing ratio deviates from the conventional value of 50:50, the known tubes are not suitable.

The two-component compositions according to the invention are preferably formulated in a two-chamber tube which has an inner chamber and an outer chamber, both of which end in a common head region (exit region). The head region is configured in such a way that the two preparations exit from the tube together as soon as pressure is exerted thereon. The configuration of this head region determines in what pattern the preparations exit from the tube.

The choice of the volumes of the individual chambers is governed by the desired ratio of the volumes of preparation (A) and preparation (B) in the two-component composition.

The preferably used two-chamber tube is characterized in particular by a particular configuration of the exit region. Here, the ratio of the chamber volumes is reflected in the cross sections of the routes defined for the part-streams. In this connection, it may be noted that the part-stream of a preparation can have a plurality of parallel branch-streams. For example, separating means can divide the cross section of the passage channel into two or more part-streams to correspond at least approximately to the ratio. In this connection, it should be noted that it is advantageous for the function of the two-chamber tubes if the different components present in the respective tube chambers each have approximately the same viscosity.

Although the invention is not, in principle, intended to be restricted in any way with regard to the pattern with which the preparations exit from the tube, it may be preferred according to the invention if the first preparation exits as the main strand and the second preparation forms a plurality of stripes running along this main strand. With regard to the number of these stripes too, the invention is not intended to be restricted. However, a number of from 2 to 4 stripes may be particularly preferred according to the invention for application reasons. In this connection, in a first embodiment, preparation (A) can form the stripes while preparation (B) forms the main strand, and in a second embodiment preparation (B) can form the stripes while preparation (A) forms the main strand.

In a further embodiment, however, it may also be preferred if the two preparations proportionally form the main strand together—one next to the other. In a further embodiment, the exit strand can consist of an inner region, formed from a first preparation, and of an outer region, formed from the second preparation, with the preparations also forming the exit strand according to their arrangement in the tube.

The quantitative ratio of preparation (A) to the amount of preparation (B) according to the invention is preferably in a range from 1:2 to 5:1, a range from 1:1 to 3:1 is particularly preferred according to the invention.

In principle, the present invention is to include every distribution of the chambers within the tube. In a first embodiment, the two individual chambers can, for example, be arranged one next to the other in an outer sheath. In an embodiment which is particularly preferred according to the invention, the two-chamber tube consists of an inner tube which is completely surrounded by an outer tube. This embodiment is characterized by an optimally constant dosing of the two preparations. Although in principle every distribution of the preparations between the chambers of the tube is to be covered according to the invention, it may be particularly preferred if preparation (A) is located in the outside tube, and preparation (B) is located in the inside tube.

The two-chamber tube is preferably manufactured from a material which is suitable for the packaging of tints and colorants of this type. Laminated aluminum has proven particularly suitable according to the invention both for the outside walls and also for the inside walls. However, tubes made of plastic laminate (PE, PET, PP) or plastic coextrudates (PE, PET, PP) are also devisable. Moreover, in one embodiment, the material of the inside tube can be chosen independently of the material of the outside tube.

A tube which has proven to be very particularly preferred according to the invention is one in which the inside tube is manufactured from aluminum laminate, which is, if appropriate, also protected by a coating, and the outside tube is manufactured either from aluminum laminate or from plastic laminate. According to the invention, aluminum laminate is understood as meaning an aluminum layer coated with plastic.

It is particularly advantageous if the shoulder region of the outside tube is strengthened with disks which have particularly good barrier properties. Here, it is advantageous to incorporate aluminum in the material of the disks.

In order to prevent the mixture from escaping during storage and the consumer having to ensure that the tube is still intact, it is advantageous to seal the exit opening with a tamper-proof seal made of aluminum or plastic, which is removed by the consumer.

Besides the components essential according to the invention, the preparations (A) and (B) can also comprise all active ingredients, additives and auxiliaries known for such preparations.

In many cases, the colorants comprise at least one surfactant, with in principle either anionic or zwitterionic, ampholytic, nonionic and cationic surfactants being suitable. In many cases, however, it has proven advantageous to choose the surfactants from anionic, zwitterionic or nonionic surfactants.

Suitable anionic surfactants in preparations according to the invention are all anionic surface-active substances suitable for use on the human body. These are characterized by a water-solubilizing, anionic group, such as, for example, a carboxylate, sulfate, sulfonate or phosphate group, and a lipophilic alkyl group having about 10 to 22 carbon atoms. In addition, glycol or polyglycol ether groups, ester, ether and amide groups, and hydroxyl groups may be present in the molecule. Examples of suitable anionic surfactants are, in each case in the form of the sodium, potassium and ammonium salts, and also the mono-, di- and trialkanolammonium salts having 2 or 3 carbon atoms in the alkanol group, linear fatty acids having 10 to 22 carbon atoms (soaps), ether carboxylic acids of the formula R—O—($CH_2$—$CH_2O$)$_x$—$CH_2$—COOH, in which R is a linear alkyl group having 10 to 22 carbon atoms and x=0 or 1 to 16, acyl sarcosides having 10 to 18 carbon atoms in the acyl group,
acyl taurides having 10 to 18 carbon atoms in the acyl group,
acyl isethionates having 10 to 18 carbon atoms in the acyl group,
sulfosuccinic mono- and dialkyl esters having 8 to 18 carbon atoms in the alkyl group and sulfosuccinic monoalkylpolyoxyethyl esters having 8 to 18 carbon atoms in the alkyl group and 1 to 6 oxyethyl groups,
linear alkanesulfonates having 12 to 18 carbon atoms,
linear alpha-olefinsulfonates having 12 to 18 carbon atoms,
alpha-sulfo fatty acid methyl esters of fatty acids having 12 to 18 carbon atoms,
alkyl sulfates and alkyl polyglycol ether sulfates of the formula R—O(CH$_2$—CH$_2$O)$_x$—SO$_3$H, in which R is a preferably linear alkyl group having 10 to 18 carbon atoms and x=0 or 1 to 12,
mixtures of surface-active hydroxysulfonates according to DE-A-37 25 030,
sulfated hydroxyalkylpolyethylene and/or hydroxyalkylenepropylene glycol ethers as in DE-A-37 23 354,
sulfonates of unsaturated fatty acids having 12 to 24 carbon atoms and 1 to 6 double bonds as in DE-A-39 26 344,
esters of tartaric acid and citric acid with alcohols, which constitute addition products of about 2–15 molecules of ethylene oxide and/or propylene oxide onto fatty alcohols having 8 to 22 carbon atoms.

Preferred anionic surfactants are alkyl sulfates, alkylpolyglycol ether sulfates and ether carboxylic acids having 10 to 18 carbon atoms in the alkyl group and up to 12 glycol ether groups in the molecule and, in particular, salts of saturated and, in particular, unsaturated C$_8$–C$_{22}$-carboxylic acids, such as oleic acid, stearic acid, isostearic acid and palmitic acid.

Nonionogenic surfactants comprise, as hydrophilic group, e.g., a polyol group, a polyalkylene glycol ether group or a combination of polyol and polyglycol ether group. Such compounds are, for example,
addition products of from 2 to 30 mol of ethylene oxide and/or 1 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group,
C$_{12}$–C$_{22}$ fatty acid mono- and diesters of addition products of from 1 to 30 mol of ethylene oxide onto glycerol,
C$_8$–C$_{22}$-alkyl mono- and oligoglycosides and ethoxylated analogs thereof, and
addition products of from 5 to 60 mol of ethylene oxide onto castor oil and hydrogenated castor oil.

Preferred nonionic surfactants are alkyl polyglycosides of the general formula R$^1$O—(Z)$_x$. These compounds are characterized by the following parameters.

The alkyl radical R$^1$ comprises 6 to 22 carbon atoms and may either be linear or branched. Preference is given to primary aliphatic radicals which are linear or methyl-branched in the 2 position. Such alkyl radicals are, for example, 1-octyl, 1-decyl, 1-lauryl, 1-myristyl, 1-cetyl and 1-stearyl. Particular preference is given to 1-octyl, 1-decyl, 1-lauryl, 1-myristyl. When using so-called "oxo alcohols" as starting materials, compounds with an uneven number of carbon atoms in the alkyl chain predominate.

The alkyl polyglycosides which can be used according to the invention can, for example, comprise only one particular alkyl radical R$^1$. Usually, however, these compounds are prepared starting from natural fats and oils or mineral oils. In this case, the alkyl radicals R present are mixtures corresponding to the starting compounds and/or corresponding to the particular work-up of these compounds.

Particular preference is given to those alkyl polyglycosides in which R$^1$ consists
essentially of C$_8$- and C$_{10}$-alkyl groups,
essentially of C$_{12}$- and C$_{14}$-alkyl groups,
essentially of C$_8$- to C$_{16}$-alkyl groups or
essentially of C$_{12}$- to C$_{16}$-alkyl groups.

Sugar building blocks Z which may be used are any mono- or oligosaccharides. Usually, sugars with 5 or 6 carbon atoms and the corresponding oligosaccharides are used. Such sugars are, for example, glucose, fructose, galactose, arabinose, ribose, xylose, lyxose, allose, altrose, mannose, gulose, idose, talose and sucrose. Preferred sugar building blocks are glucose, fructose, galactose, arabinose and sucrose; glucose is particularly preferred.

The alkyl polyglycosides which can be used according to the invention comprise, on average, 1.1 to 5 sugar units. Alkyl polyglycosides with x values of from 1.1 to 1.6 are preferred. Very particular preference is given to alkyl glycosides in which x is 1.1 to 1.4.

Besides their surfactant effect, the alkyl glycosides can also serve to improve the fixing of scent components on the hair. Thus, if an effect of the perfume oil on the hair which lasts beyond the duration of the hair treatment is desired, the person skilled in the art will preferably have recourse to this class of substance as a further ingredient of the preparations according to the invention.

The alkoxylated homologs of the specified alkyl polyglycosides can also be used according to the invention. These homologs can on average comprise up to 10 ethylene oxide and/or propylene oxide units per alkyl glycoside unit.

In addition, zwitterionic surfactants can be used, in particular, as cosurfactants. "Zwitterionic surfactants" is the term used to refer to those surface-active compounds which carry at least one quaternary ammonium group and at least one —COO$^{(-)}$ or —SO$_3^{(-)}$ group in the molecule. Particularly suitable zwitterionic surfactants are the so-called betaines, such as the N,N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethyl hydroxyethylcarboxymethylglycinate. A preferred zwitterionic surfactant is the fatty acid amide derivative known under the INCI name Cocamidopropyl Betaine.

Likewise particularly suitable as cosurfactants are ampholytic surfactants. Ampholytic surfactants are understood as meaning those surface-active compounds which, apart from a C$_8$–C$_{18}$-alkyl or acyl group, comprise at least one free amino group and at least one —COOH or —SO$_3$H group in the molecule and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and C$_{12-18}$-acylsarcosine.

The cationic surfactants used according to the invention are, in particular, those of the quaternary ammonium compound type, the ester quat type and the amidoamine type.

Preferred quaternary ammonium compounds are ammonium halides, in particular chlorides and bromides, such as alkyltrimethylammonium chlorides, dialkyldimethylammonium chlorides and trialkylmethylammonium chlorides, e.g., cetyltrimethylammonium chloride and, stearyltrimethylammonium chloride, distearyldimethylammonium chloride, lauryldimethylammonium chloride, lauryldimethylbenzylammonium chloride and tricetylmethylammonium chloride, and the imidazolium compounds known under the INCI names Quaternium-27 and Quaternium-83. The long alkyl chains of the above-mentioned surfactants preferably have 10 to 18 carbon atoms.

Ester quats are known substances which comprise both at least one ester function and also at least one quaternary ammonium group as structural element. Preferred ester quats are quaternized ester salts of fatty acids with triethanolamine, quaternized ester salts of fatty acids with diethanolalkylamines and quaternized ester salts of fatty acids with 1,2-dihydroxypropyldialkylamines. Such products are sold, for example, under the trade names Stepantex®, Dehyquart® and Armocare®. The products Armocare® VGH-70, an N,N-bis(2-palmitoyloxyethyl)dimethylammonium chloride, and Dehyquart® F-75 and Dehyquart® AU-35 are examples of such ester quats.

The alkylamidoamines are usually prepared by amidation of natural or synthetic fatty acids and fatty acid segments with dialkylaminoamines. A compound from this group of substances which is particularly suitable according to the invention is the stearamidopropyldimethylamine available commercially under the name Tegoamid® S 18.

Further cationic surfactants which can be used according to the invention are the quaternized protein hydrolyzates.

Likewise suitable according to the invention are cationic silicone oils, such as, for example, the commercially available products Q2-7224 (manufacturer: Dow Corning; a stabilized trimethylsilylamodimethicone), Dow Corning 929 Emulsion (comprising a hydroxyamino-modified silicone, which is also referred to as amodimethicone), SM-2059 (manufacturer: General Electric), SLM-55067 (manufacturer: Wacker) and Abil®-Quat 3270 and 3272 (manufacturer: Th. Goldschmidt; diquaternary polydimethylsiloxanes, Quaternium-80).

One example of a quaternary sugar derivative which can be used as cationic surfactant is the commercial product Glucquat®100, according to INCI nomenclature a "Lauryl Methyl Gluceth-10 Hydroxypropyl Dimonium Chloride."

The compounds with alkyl groups used as surfactant may each be individual substances. However, it is usually preferred to start from natural vegetable or animal raw materials when preparing these substances, resulting in mixtures of substances with varying alkyl chain lengths which depend on the particular raw material.

The surfactants which constitute addition products of ethylene oxide and/or propylene oxide onto fatty alcohols or derivatives of these addition products and may be used are either products with a "normal" homolog distribution, or those with a narrowed homolog distribution. "Normal" homolog distribution is understood here as meaning mixtures of homologs which are obtained when reacting fatty alcohol and alkylene oxide using alkali metals, alkali metal hydroxides or alkali metal alkoxides as catalysts. Narrowed homolog distributions, by contrast, are obtained if, for example, hydrotalcites, alkaline earth metal salts of ether carboxylic acids, alkaline earth metal oxides, hydroxides or alkoxides are used as catalysts. The use of products with a narrowed homolog distribution may be preferred.

In addition, the colorants according to the invention can comprise further active ingredients, auxiliaries and additives, such as, for example, nonionic polymers, such as, for example, vinylpyrrolidone/vinyl acrylate copolymers, polyvinylpyrrolidone and vinylpyrrolidone/vinyl acetate copolymers and polysiloxanes, cationic polymers, such as quaternized cellulose ethers, polysiloxanes with quaternary groups, dimethyldiallylammonium chloride polymers, acrylamide/dimethyldiallylammonium chloride copolymers, dimethylaminoethyl methacrylate/vinylpyrrolidone copolymers quaternized with diethyl sulfate, vinylpyrrolidone/imidazolinium methochloride copolymers and quaternized polyvinyl alcohol, zwitterionic and amphoteric polymers, such as, for example, acrylamidopropyltrimethylammonium chloride/acrylate copolymers and octylacrylamide/methyl methacrylate/tert-butylaminoethyl methacrylate/2-hydroxypropyl methacrylate copolymers, anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butylacrylamide terpolymers, thickeners, such as agar-agar, guar gum, alginates, xanthan gum, gum arabic, karaya gum, carob seed flour, linseed gums, dextrans, cellulose derivatives, e.g. methylcellulose, hydroxyalkylcellulose and carboxymethylcellulose, starch fractions and derivatives, such as amylose, amylopectin and dextrins, clays, such as, for example, bentonite or completely synthetic hydrocolloids such as, for example, polyvinyl alcohol, structurants, such as maleic acid and lactic acid, hair conditioning compounds, such as phospholipids, for example soya lecithin, egg lecithin and cephalins, protein hydrolyzates, in particular elastin, collagen, keratin, milk protein, soya protein and wheat protein hydrolyzates, condensation products thereof with fatty acids, and quaternized protein hydrolyzates, perfume oils, dimethyl isosorbide and cyclodextrins, solvents and solubility promoters, such as ethanol, isopropanol, ethylene glycol, propylene glycol, glycerol and diethylene glycol, active ingredients which improve the fiber structure, in particular mono-, di- and oligosaccharides, such as, for example, glucose, galactose, fructose, fruit sugar and lactose, quaternized amines, such as methyl-1-alkylamidoethyl-2-alkylimidazolium methosulfate, antifoams, such as silicones, dyes for coloring the composition, antidandruff active ingredients, such as piroctone olamine, zinc omadine and climbazole, photoprotective agents, in particular derivatized benzophenones, cinnamic acid derivatives and triazines, substances for adjusting the pH, such as, for example, customary acids, in particular food acids and bases, active ingredients, such as allantoin, pyrrolidonecarboxylic acids and salts thereof, and bisabolol, vitamins, provitamins and vitamin precursors, in particular those of groups A, $B^3$, $B^5$, $B^6$, C, E, F and H, plant extracts, such as the extracts from green tea, oak bark, stinging nettle, hamamelis, hops, chamomile, burdock root, horsetail, hawthorn, lime blossom, almond, aloe vera, spruce needle, horse chestnut, sandalwood, juniper, coconut, mango, apricot, lemon, wheat, kiwi, melon, orange, grapefruit, sage, rosemary, birch, mallow, lady's smock, wild thyme, yarrow, thyme, melissa, restharrow, coltsfoot, marshmallow, meristem, ginseng and ginger root, cholesterol, consistency regulators such as sugar esters, polyol esters or polyol alkyl ethers, fats and waxes, such as spermaceti, beeswax, montan wax and paraffins, fatty acid alkanolamides, complexing agents, such as EDTA, NTA, β-alaninediacetic acid and phosphonic acids, swelling and penetration substances, such as glycerol, propylene glycol monoethyl ether, carbonates, hydrogencarbonates, guanidines, ureas, and primary, secondary and tertiary phosphates, opacifiers, such as latex, styrene/PVP and styrene/acrylamide copolymers, pearlizing agents, such as ethylene glycol mono- and distearate, and PEG-3 distearate, preservatives, stabilizers for hydrogen peroxide and other oxidizing agents, propellants, such as propane-butane mixtures, $N_2O$, dimethyl ether, $CO_2$ and air, antioxidants.

With regard to further optional components and the amounts used of these components, reference is made expressly to the relevant handbooks known to the person skilled in the art, e.g., Kh. Schrader, Grundlagen und Rezepturen der Kosmetika [Fundamentals and formulations of cosmetics], 2nd edition, Hüthig Buch Verlag, Heidelberg, 1989.

According to the invention, the preparations (A) and (B) comprise the components essential to the invention preferably in a suitable aqueous, alcoholic or aqueous-alcoholic carrier. For the purposes of coloring hair, such carriers are, for example, creams, emulsions, gels and also surfactant-containing foaming solutions, such as, for example, shampoos or other preparations which are suitable for use on the hair.

For the purposes of the present invention, aqueous-alcoholic solutions is understood as meaning aqueous solutions comprising 3 to 70% by weight of $C_1$–$C_4$-alcohol, in particular ethanol or isopropanol. The compositions according to the invention can additionally comprise further organic solvents, such as, for example, methoxybutanol, benzyl alcohol, ethyl diglycol or 1,2-propylene glycol. Preference is given here to all water-soluble organic solvents.

In addition, the two-component compositions according to the invention can comprise a reducing agent. Examples of reducing agents preferred according to the invention are sodium sulfite, ascorbic acid, thioglycolic acid and derivatives thereof, sodium thionite, alkali metal citrate salts and N-acetyl-L-cysteine. Very particularly preferred reducing agents are alkali metal citrate salts, in particular sodium citrate, and N-acetyl-L-cysteine. N-Acetyl-L-cysteine is a very particularly preferred reducing agent.

Futhermore, the compositions according to the invention can comprise alkalinizing agents, usually alkali metal or alkaline earth metal hydroxides, ammonia or organic amines. Preferred alkalinizing agents are monoethanolamine, monoisopropanolamine, 2-amino-2-methylpropanol, 2-amino-2-methyl-1,3-propanediol, 2-amino-2-ethyl-1,3-propanediol, 2-amino-2-methylbutanol and triethanolamine, and also alkali metal and alkaline earth metal hydroxides. Especially monoethanolamine, triethanolamine and 2-amino-2-methylpropanol and 2-amino-2-methyl-1,3-propanediol are preferred within this group. The use of ω-amino acids, such as ω-aminocaproic acid, as alkalinizing agent is also possible.

In addition, the two-component compositions according to the invention can comprise pearlescent pigments for coloring in preparation (A) and/or preparation (B). Pearlescent pigments preferred according to the invention are natural pearlescent pigments, such as, for example, pearl essence (guanine/hypoxanthine mixed crystals from fish scales) or mother of pearl (from ground mussel shells), monocrystalline pearlescent pigments, such as, for example, bismuth oxychloride, and pearlescent pigments based on mica or mica/metal oxide. The last-mentioned pearlescent pigments are provided with a metal oxide coating. Use of the pearlescent pigments achieves shine and, if appropriate, additionally color effects in the two-component compositions according to the invention. However, the imparting of color through the pearlescent pigments used in the two-component compositions does not influence the color result of the coloration of the keratin fibers.

Pearlescent pigments based on mica and on mica/metal oxide are likewise preferred according to the invention. Mica is a type of sheet silicate. The most important representatives of these silicates are muscovite, phlogopite, paragonite, biotite, lepidolite and margarite. To produce the pearlescent pigments in combination with metal oxides, the mica, predominantly muscovite or phlogopite, is coated with a metal oxide. Suitable metal oxides are, inter alia, $TiO_2$, $Cr_2O_3$ and $Fe_2O_3$. Appropriate coating produces interference pigments, and colored luster pigments as pearlescent pigments according to the invention. Besides a glittering optical effect, these types of pearlescent pigment additionally have color effects. Furthermore, the pearlescent pigments which can be used according to the invention can also comprise a colored pigment that is not derived from a metal oxide.

The particle size of the preferably used pearlescent pigments is preferably between 1.0 and 100 μm, particularly preferably between 5.0 and 60.0 μm.

Particularly preferred pearlescent pigments are pigments which are marketed by Merck under the trade names Colorona®, where the pigments Colorona® red-brown (47–57% by weight of muscovite mica ($KH_2(AlSiO_4)_3$), 43–50% by weight of $Fe_2O_3$ (INCI: Iron Oxides Cl 77491), <3% by weight of $TiO_2$ (INCI: Titanium Dioxide Cl 77891), Colorona® Blackstar Blue (39–47% by weight of muscovite mica ($KH_2(AlSiO_4)_3$), 53–61% by weight of $Fe_3O_4$ (INCI: Iron Oxides Cl 77499), Colorona® Siena Fine (35–45% by weight of muscovite mica ($KH_2(AlSiO_4)_3$), 55–65% by weight of $Fe_2O_3$ (INCI: Iron Oxides Cl 77491), Colorona® Aborigine Amber (50–62% by weight of muscovite mica ($KH_2(AlSiO_4)_3$), 36–44% by weight of $Fe_3O_4$ (INCI: Iron Oxides Cl 77499), 2–6% by weight of $TiO_2$ (INCI: Titanium Dioxide Cl 77891), Colorona® Patagonian Purple (42–54% by weight of muscovite mica ($KH_2(AlSiO4)_3$), 26–32% by weight of $Fe_2O_3$ (INCI: Iron Oxides Cl 77491), 18–22% weight of $TiO_2$ (INCI: Titanium Dioxide Cl 77891), 2–4% by weight of Prussian Blue (INCI: Ferric Ferrocyanide Cl 77510), Colorona® Chameleon (40–50% by weight of muscovite mica ($KH_2(AlSiO_4)$3), 50–60% by weight of $Fe_2O_3$ (INCI: Iron Oxides Cl 77491) and Silk® Mica (>98% by weight of muscovite mica ($KH_2(AlSiO_4)_3$) are very particularly preferred.

With regard to the pearlescent pigments which can used in the two-component compositions according to the invention, reference is also expressly made to the monographs Inorganic Pigments, Chemical technology review No. 166,1980, pages 161–173 (ISBN 0-8155-0811-5) and Industrial Inorganic Pigments, 2nd edition, Weinheim, VCH, 1998, pages 211–231.

The actual colorant is obtained by thoroughly mixing the two preparations (A) and (B) exiting from the tube. This thorough mixing of the preparations (A) and (B) emerging separately from the tube can take place either prior to application to the fibers in a separate step, or as a secondary effect while incorporating the exit strand into the fibers. The resulting ready-to-use hair coloring preparation should preferably have a pH in the range from 6 to 12. Unless noted otherwise, within the scope of the present disclosure, the data for the pH is to be understood as meaning the pH at 25° C. Particular preference is given to applying the hair colorant in an alkali medium. The application temperatures can be in a range between 15 and 40° C. After a contact time of from 5 to 45 minutes, the hair colorant is removed from the hair to be colored by rinsing. There is no need for afterwashing with a shampoo if a carrier with a high content of surfactant, e.g., a coloring shampoo, has been used.

The preparations (A) and (B) according to the invention preferably have viscosities in the range from 2,000 to 200,000 mPas, in particular from 5,000 to 50,000 mPas (Brookfield viscometer, spindle No. 4, 20 rpm, 20° C.). In this way, it is ensured that the two-component composition has good miscibility and that the exit sample has sufficient stability.

The present invention secondly provides a method of coloring keratin fibers, in particular human hair, where a two-component composition according to the invention is squeezed out of the tube, the resulting application preparation is applied to the fibers and, after a contact time, is rinsed out again.

The examples below are intended to illustrate the subject matter of the present invention without limiting it in any way.

Working Examples.

The following formulations were prepared. Unless noted otherwise, the quantitative data is in percent by weight.

Formulations of Preparation (A).

|  | Coloring cream | | | | | |
| --- | --- | --- | --- | --- | --- | --- |
| Raw materials | A | B | C | D | E | F |
| Texapon ® K14 S 70° C. | 2.8 | 2.8 | 2.8 | 2.8 | 2.8 | 2.8 |
| Phopholipid ® EFA | 1.0 | — | — | 1.0 | — | — |
| Plantacare ® 1200 UP | 2.0 | 2.0 | — | — | — | — |
| Lamesoft ® PO65 | — | — | — | 2.0 | 2.0 | — |
| Akypo Soft ® 45 NV | 10.0 | 8.0 | 10.0 | 10.0 | 8.0 | 10.0 |
| Hydrenol ® D | 8.0 | 8.0 | 8.0 | 8.0 | 8.0 | 8.0 |
| Kokoslorol ® | 2.0 | 2.0 | 2.0 | 2.0 | 2.0 | 2.0 |
| Eutanol ® G | 1.0 | 1.5 | 1.0 | 1.0 | 1.5 | 1.0 |
| Eumulgin ® B1 | 0.5 | 0.5 | 0.5 | 0.5 | 0.5 | 0.5 |
| Eumulgin ® B2 | 0.5 | 0.5 | 0.5 | 0.5 | 0.5 | 0.5 |
| KOH 50% strength | 0.7 | 1.0 | 2.0 | 0.7 | 1.0 | 2.0 |
| Color powder mixture | a | b | c | a | b | C |
| Water, demineralized | to 100 | to 100 | to 100 | to 100 | to 100 | To 100 |
| Ascorbic acid | 0.1 | 0.05 | 0.1 | 0.1 | 0.05 | 0.1 |
| Sodium sulfite | 0.15 | 0.2 | 0.3 | 0.1 | 0.2 | 0.3 |
| Ammonia, 25% strength | 6.0 | 8.0 | 6.0 | 6.0 | 8.0 | 6.0 |
| Turpinal ® SL | 0.2 | 0.2 | 0.2 | 0.2 | 0.2 | 0.2 |
| Mirapol ® A 15 | 0.2 | — | 0.2 | 0.2 | — | 0.2 |
| Perfume | 0.25 | 0.25 | 0.25 | 0.25 | 0.25 | 0.25 |

|  | Coloring cream | | |
| --- | --- | --- | --- |
| Raw materials: | G | H | I |
| Texapon ® NSO | 7.0 | 7.0 | 7.0 |
| Dehyton ® K | 5.0 | 5.0 | 5.0 |
| Prisorine ® 3501 | 2.0 | 2.0 | 2.0 |
| Edenor ® C14 | 0.5 | 0.5 | 0.5 |
| Phospholipid EFA ® | 1.0 | 1.0 | — |
| Plantacare | 0.5 | | 0.5 |
| Hydrenol ® D | 8.0 | 8.0 | 8.0 |
| Kokoslorol ® | 2.5 | 2.5 | 2.5 |
| Eumulgin ® B1 | 0.5 | 0.5 | 0.5 |
| Eumulgin ® B2 | 0.5 | 0.5 | 0.5 |
| KOH 50% strength | 0.7 | 1.0 | 2.0 |
| Color powder mixture | a | B | c |
| Water, demineralized | to 100 | to 100 | to 100 |
| Sodium sulfite | 0.15 | 0.2 | 0.3 |
| Ascorbic acid | 0.1 | 0.05 | 0.1 |
| Ammonia 25% strength | 6.0 | 8.0 | 6.0 |
| Turpinal ® SL | 0.2 | 0.2 | 0.2 |
| Mirapol ® A 15 | 0.2 | — | — |
| Perfume | 0.3 | 0.3 | 0.3 |

The following color powder mixtures a, b and c were used in the coloring creams A to I:

| Raw material name: | |
| --- | --- |
| | Color powder mixture a |
| p-Tolylenediamine sulfate | 0.90 |
| Resorcinol | 0.20 |

-continued

| Raw material name: | |
|---|---|
| m-Aminophenol | 0.06 |
| 4-Chlororesorcinol | 0.15 |
| Coloration | Blond |
| Color powder mixture b | |
| p-Tolylenediamine sulfate | 0.20 |
| 1-(2-Hydroxyethyl)-4,5-diaminopyrazole | 1.50 |
| m-Aminophenol | 0.05 |
| 5-Amino-2-methylphenol | 0.80 |
| Coloration | Red |
| Color powder mixture c | |
| p-Tolylenediamine sulfate | 2.20 |
| Resorcinol | 0.30 |
| 2,4-Diaminophenoxyethanol hydrochloride | 1.70 |
| Coloration | Blue-black |

Formulations of Preparation (B).

| Raw material | |
|---|---|
| | Oxidizing agent preparation B1 |
| Cetylstearyl alcohol | 8.0 |
| Eumulgin ® B2 | 2.5 |
| Dehyquart ® B | 1.0 |
| Dipicolinic acid | 0.1 |
| Paraffin oil DAB 7 | 0.3 |
| Turpinal ® SL | 0.4 |
| 1,2-propylene glycol | 0.4 |
| Sodium benzoate | 0.04 |
| Hydrogen peroxide 50% | 12.0 |

-continued

| Raw material | |
|---|---|
| Potassium hydroxide solution 50% strength | To pH 3.5 |
| Water dist. | To 100 |
| | Oxidizing agent preparation B2 |
| Stearyl stearate | 2.00 |
| Cetyl alcohol | 6.00 |
| Ceteth-20 | 4.00 |
| Propylene glycol | 1.00 |
| Sodium pyrophosphate | 0.01 |
| Phosphoric acid | to pH 3 |
| Hydrogen peroxide 50% | 18.0 |
| Water | to 100 |

Coloration.

The coloring creams A to I were in each case formulated in the ratio 1:1 with the oxidation cream B1, or in the ratio 3:1 with the oxidation cream B2 in a two-chamber tube. Here, the inside tube contained preparation (B), and the outside tube contained preparation (A). The entire tube consisted of aluminum laminate.

Directly prior to application, the two-component composition was applied directly to human hair (Kerling natural white) from the two-chamber tube, massaged in, left to act at room temperature for 30 minutes and then rinsed out. After drying the hair, intense blond, red or blue-black nuances were achieved.

List of the Commercial Products Used.

The commercial products used in the course of the examples are defined as follows:

| | |
|---|---|
| Akypo Soft 45 NV ® | Lauryl alcohol-4.5-EO acetic acid sodium salt (min. 21% active substance content; INCI name: Sodium Laureth-6 Carboxylate) (Chem-Y) |
| Dehyquart ® B | Stearyltrimethylammonium chloride (about 60–66% active substance content; INCI name: Steartrimonium Chloride) (Cognis) |
| Dehyton ® K | N,N-Dimethyl-N-($C_{8-18}$-cocoamidopropyl)ammonium acetobetaine (about 30% active substance; INCI name: Aqua (Water), Cocamidopropyl Betaine) (Cognis) |
| Edenor ® C14 | Myristic acid (INCI name: MYRISTIC ACID) (Cognis) |
| Eumulgin ® B1 | Cetylstearyl alcohol with about 12 EO units (INCI name: Ceteareth-12) (Cognis) |
| Eumulgin ® B2 | Cetylstearyl alcohol with about 20 EO units (INCI name: Ceteareth-20) (Cognis) |
| Eutanol ® G | 2-Octyldodecyl alcohol (INCI name: Octyldodecanol) (Cognis) |
| Hydrenol ® D | $C_{16-18}$ fatty alcohol (INCI name: Cetearyl alcohol) (Cognis) |
| Kocoslorol ® | $C_{12-18}$ fatty alcohol (INCI name: Coconut Alcohol) (Cognis) |
| Lamesoft ® PO65 | Alkyl polyglucoside oleic acid monoglyceride mixture (about 65–70% solids; INCI name: Coco-Glucoside Glycerol Oleate, Aqua (Water)) (Cognis) |
| Mirapol ® A 15 | Poly[N-(3-(dimethylammonium)propyl]-N'-[3-ethyl-eneoxyethylenedimethylammonium)propyl]urea dichloride (about 64% solids in water; INCI name: Polyquaternium-2) (Rhodia) |
| Phopholipid ® EFA | (INCI name: Linoleamidopropyl PG-Dimonium Chloride Phosphate) (Uniqema) |
| Plantcare ® 1200 UP | $C_{12-16}$-fatty alcohol 1.4-glucoside (about 50–53% active substance content; INCI name: Lauryl Glucoside, Aqua (Water)) (Cognis) |
| Prisorine ® 3501 | Isooctadecanoic acid (INCI name: Isostearic Acid) (Unichema) |
| Texapon ® K 14 S 70 C | Lauryl myristyl ether sulfate sodium salt (about 68% to 73% active substance content; INCI name: Sodium Myreth Sulfate) (Cognis) |

-continued

| | |
|---|---|
| Texapon ® NSO | Lauryl ether sulfate, sodium salt (about 27.5% active substance; INCI name: Sodium Laureth Sulfate) (Cognis) |
| Turpinal ® SL | 1-Hydroxyethane-1,1-diphosphonic acid (about 58% to 61% active substance content; INCI name: Etidronic Acid, Aqua (Water)) (Solutia) |

The invention claimed is:

1. A two-component composition for coloring keratinous fibers comprising a first preparation (A) comprising at least one oxidation dye precursor and a second preparation (B) comprising at least one oxidizing agent, wherein the first and second preparations are packaged separately in a two chamber tube having an inner and outer chamber and a common exit region wherein the exit region is configured in such a way that the first preparation exits as the main strand and the second preparation forms a plurality of stripes running along the main strand when pressure is exerted on the tube and wherein the ratio of preparation (A) to preparation (B) is in a range from 1:1 to 3:1.

2. The composition of claim 1 wherein preparation (A) is comprised of at least one developer component.

3. The composition of claim 1 wherein preparation (A) is comprised of at least one coupler component.

4. The composition of claim 1 wherein preparation (A) further comprises at least one precursor of a nature-analogous dye.

5. The composition of claim 1 wherein preparation (A) further comprises at least one direct dye.

6. The composition of claim 1 wherein the oxidizing agent is hydrogen peroxide or its addition products onto urea, melamine, and sodium borate.

7. The composition of claim 1 wherein tho oxidizing agent is an enzyme.

8. The composition of claim 1 wherein the oxidizing agent is an oxidation catalyst.

9. A two-chamber tube comprising a first chamber comprising a preparation (A) comprising at least one oxidation dye precursor and a second compartment comprising a preparation (B) comprising at least one oxidizing agent wherein the first and second preparations are packaged separately in a two chamber tube having on inner and outer chamber and a common exit region wherein the exit region is configured in such a way that the first preparation exits as the main strand and the second preparation forms a plurality of stripes running along the main strand when pressure is exerted on the tube and wherein the preparations are emitted from the exit region at a volume ratio of (A) to (B) corresponding to 1:1 to 3:1.

10. The tube of claim 9 wherein the preparations are emitted from the exit region in a stripe-like pattern.

11. A method for coloring keratinic fibers in particular human hair comprising contacting the fibers with preparation (A) and (B) from the exit region of claim 1 for a period of time and then removing the preparations from the fibers.

12. The method of claim 11 wherein the preparations are removed by rinsing.

* * * * *